United States Patent
Hoque et al.

(10) Patent No.: US 9,541,521 B1
(45) Date of Patent: Jan. 10, 2017

(54) ENHANCED SENSITIVITY ION SENSING DEVICES

(71) Applicant: FREESCALE SEMICONDUCTOR, INC., Austin, TX (US)

(72) Inventors: Md M. Hoque, Gilbert, AZ (US);
Weize Chen, Phoenix, AZ (US);
Patrice M. Parris, Phoenix, AZ (US)

(73) Assignee: NXP USA, Inc., Austin, TX (US)

( * ) Notice: Subject to any disclaimer, the term of this patent is extended or adjusted under 35 U.S.C. 154(b) by 0 days.

(21) Appl. No.: 14/928,877

(22) Filed: Oct. 30, 2015

(51) Int. Cl.
*G01N 27/414* (2006.01)
*G01N 27/333* (2006.01)

(52) U.S. Cl.
CPC .......... *G01N 27/333* (2013.01); *G01N 27/414* (2013.01)

(58) Field of Classification Search
CPC .............................. G01N 27/333; G01N 27/414
See application file for complete search history.

(56) References Cited

U.S. PATENT DOCUMENTS

| | | |
|---|---|---|
| 4,103,227 A | 7/1978 | Zemel |
| 5,111,221 A | 5/1992 | Fare et al. |
| 5,770,509 A | 6/1998 | Yu et al. |
| 5,814,280 A | 9/1998 | Tomita et al. |
| 6,387,724 B1 | 5/2002 | Walker |
| 7,057,241 B2 | 6/2006 | Ojala |
| 7,740,805 B2 | 6/2010 | Parris |
| 8,283,736 B2 | 10/2012 | Kang et al. |
| 8,421,082 B1 * | 4/2013 | Yang .................... B81C 1/00246 257/288 |
| 8,482,304 B2 | 7/2013 | Sheu et al. |
| 8,776,274 B2 | 7/2014 | Parris et al. |
| 8,858,782 B2 * | 10/2014 | Fife .................... G01N 27/4148 205/792 |
| 8,878,257 B2 | 11/2014 | Parris et al. |

(Continued)

FOREIGN PATENT DOCUMENTS

WO  2011049428 A1  4/2011

OTHER PUBLICATIONS

Chapman, R. et al., "Comparison of Methods to Bias Fully Depleted SOI-Based MOSFET Nanoribbon pH Sensors", IEEE Transactions on Electron Devices, vol. 58, No. 6, Jun. 2011, pp. 1752-1760.

(Continued)

*Primary Examiner* — Christine Enad (57) ABSTRACT

A mechanism is provided for enhancing the sensitivity of an ion-sensitive semiconductor device by creating a second gate coupled to a sense plate that can improve the amount of charge brought to the ion-sensitive semiconductor device conductivity modulated region (e.g., a channel region of an ISFET). This is accomplished by utilizing a buried dielectric layer associated with the ion-sensitive semiconductor device conductivity modulated region as the second gate dielectric. The buried dielectric layer is coupled to the sense plate using an isolated well region as a conductor that is coupled to metal layers extending to the sense plate. Some embodiments further use the buried dielectric layer as the sole gate dielectric for the semiconductor device, thereby allowing the traditional gate dielectric region to be coupled to a protection diode. This protection diode then protects the gate dielectric from plasma induced damage and electrostatic discharge.

20 Claims, 8 Drawing Sheets

(56) References Cited

U.S. PATENT DOCUMENTS

| | | | |
|---|---|---|---|
| 8,940,569 B2 | 1/2015 | Bedell et al. | |
| 9,023,189 B2* | 5/2015 | Rothberg | C12Q 1/6869 205/775 |
| 2010/0137143 A1* | 6/2010 | Rothberg | C12Q 1/6874 506/2 |
| 2011/0204455 A1* | 8/2011 | Kang | G01N 27/4148 257/414 |
| 2013/0217587 A1* | 8/2013 | Rothberg | C12Q 1/6869 506/2 |
| 2014/0225166 A1* | 8/2014 | Ellis-Monaghan | G01N 27/414 257/253 |
| 2015/0171018 A1* | 6/2015 | Hoque | H01L 23/552 257/253 |

OTHER PUBLICATIONS

Chern, G. et al., "Temperature Dependence of the Gate-Controlled Portion of Ion-Controlled Diodes", IEEE Transactions on Electron Devices, vol. 29, Issue 1, Jan. 1982, pp. 115-123.

Fernandes, P. et al., "Effects of Fluid Media on Ultra-Thin SOI Based pH Sensors", International Semiconductor Device Research Symposium, Dec. 9-11, 2009, pp. 1-2.

Kwoon, H. et al., "The Characteristics of H+ Ion-Sensitive Transistor Driving With MOS Hybrid Mode Operation", IEEE Electron Device Letters, vol. 29, No. 10, Oct. 2008, pp. 1138-1141.

Park, M., et al., "High Q Microwave Inductors in CMOS Double-Metal Technology and Its Substrate Bias Effects for 2 GHz RF ICs Application", International Electron Devices Meeting, 1997, pp. 59-62.

Wen, C. et al., "Gate-Controlled Diodes for Ionic Concentration Measurement", IEEE Transactions on Electron Devices, vol. 26, Issue 12, Dec. 1979, pp. 1945-1951.

Wen, C. et al., "Ion Controlled Diodes (ICD)", 1978 International Electron Devices Meeting, vol. 24, pp. 108-111.

Yadav, J. et al., "Simulation and Characterization of Dual-Gate SOI MOSFET, On-chip Fabricated with ISFET", 19th International Symposium on VLSI Design and Test (VDAT), Jun. 26-29, 2015, pp. 1-5.

Yuan, H. et al., "Novel Biosensor Based on MOSFET-BJT Hybrid Mode of Gated Lateral Bipolar Junction Transistor for C-reactive Protein Detection", 2012 Third International Conference on Intelligent Systems, Modeling and Simulation (ISMS), pp. 756-759.

Yuan, H. et al., "Gated Lateral BJT Gas Sensor for Toluene Gas Detection Under Room Temperature Condition", 2012 IEEE Sensors, pp. 1-4.

* cited by examiner

ENHANCED SENSITIVITY ION SENSING DEVICES

BACKGROUND

Field

This disclosure relates generally to ion sensing semiconductor devices, and more specifically, to a mechanism for enhancing sensitivity of ion sensing devices made using silicon on insulator techniques.

Related Art

Ion Sensitive Field Effect Transistors (ISFETs) are often used to sense a concentration of a target ion or molecule in an electrolytic solution. In early ISFET designs, the fluid being sensed was often in intimate contact with the gate dielectric, or separated from the gate dielectric by an ion-sensitive membrane. More current ISFET structures are made using CMOS process flows to create relatively low-cost devices with improved manufacturability. A typical CMOS ISFET includes a sense plate and a CMOS transistor, which includes a floating gate that is coupled to the sense plate. As is typical with a CMOS transistor, the gate is electrically isolated from the transistor channel through a gate dielectric.

In order to measure the ionic concentration, the sense plate interacts with the solution, either directly or through an ion-sensitive material formed on the sense plate, where a reaction can take place between the sense plate material and the ions. Dimensions of the sense plate are typically on the order of 100 square microns. The larger the sense plate area, the higher the sensitivity of the device. But the sense plate is a significant contributor to the size of an ISFET device, and thus larger sense plate areas increase the size of the ISFET device.

In addition, during fabrication of a typical CMOS ISFET, once the gate dielectric is formed, it is susceptible to damage, particularly plasma-induced damage from fabrication processes in which plasmas are present (e.g., during formation of metal layers coupled to the ISFET gate). These processes include, for example, plasma etching, plasma deposition, and the like. Even after fabrication, the gate dielectric may be susceptible to damage from electrostatic discharge (ESD) events or other situations in which the breakdown voltage of the gate dielectric is exceeded.

There is therefore a need for improved ISFET devices that provide enhanced sensitivity to ionic concentration without increasing the dimensions of the sense plate, and which also have decreased susceptibility to plasma-induced damage and electrostatic discharge.

BRIEF DESCRIPTION OF THE DRAWINGS

The present invention may be better understood, and its numerous objects, features, and advantages made apparent to those skilled in the art by referencing the accompanying drawings.

The use of the same reference symbols in different drawings indicates identical items unless otherwise noted. The figures are not necessarily drawn to scale.

DETAILED DESCRIPTION

Embodiments of the present invention provide a mechanism for enhancing the sensitivity of an ion-sensitive semiconductor device (e.g., an ISFET) by creating a second gate coupled to the sense plate that can improve the amount of charge brought to the conductivity modulated region (e.g., transistor channel). This is accomplished by utilizing a buried dielectric layer associated with the ISFET channel region as the second transistor gate dielectric. The buried dielectric layer is coupled to the sense plate using an isolated well region as a conductor that is coupled to metal layers extending to the sense plate. Some embodiments further use the buried dielectric layer as the sole gate dielectric for the semiconductor device, thereby allowing the traditional gate dielectric region to be coupled to a protection diode. This protection diode then protects the gate dielectric from plasma induced damage and electrostatic discharge.

Figure 1:
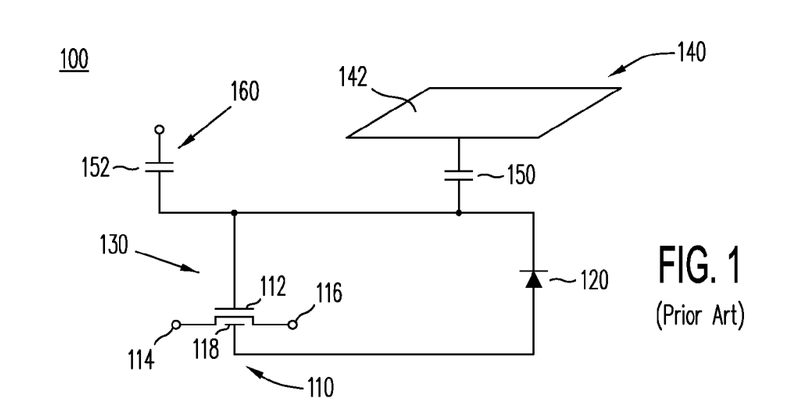
FIG. 1 is a simplified circuit representation of a traditional n-channel ISFET 100 with a protection diode 120.

FIG. 1 is a simplified circuit representation of a traditional n-channel ISFET 100 with a protection diode 120. More specifically, ISFET 100 includes an n-channel insulated-gate field effect transistor (IGFET) 110, a floating gate structure 130, a sense plate structure 140, and a protection diode 120. IGFET 110 includes a gate 112, a source region, a drain region, and a body region 118. The source and drain regions are electrically coupled to source and drain contacts 114, 116, respectively.

Gate 112 forms a portion of floating gate structure 130, which also includes one or more conductive structures that are capacitively coupled (as indicated by capacitor 150) with sense plate structure 140. Sense plate structure 140 includes a sense plate 142 (e.g., a metal plate) configured to sense the concentration of a target ion or molecule in a fluid adjacent to the sense plate 142, and additional conductive structures that facilitate the capacitive coupling between the sense plate structure 140 and the floating gate structure 130. In general, during operation of the ISFET, a concentration of a target ion or molecule within the fluid results in a corresponding electrical bias of the floating gate structure 130. More specifically, the gate bias affects the conductivity of the channel, which may result in a current signal between the source and drain contacts 114, 116 that is dependent upon the target ion or molecule concentration within the fluid. Detection circuitry (not illustrated) coupled to the source and/or drain contacts 114, 116 may determine the target ion or molecule concentration within the fluid based on the current signal.

FIG. 1 also provides a protection diode 120 to reduce damage associated with electrostatic discharge or plasma induced damage. Protection diode 120 includes a cathode coupled to the floating gate structure 130 and an anode coupled to the body region 118 of IGFET 110. In alternate structures, protection diode 120 may have an anode coupled to another region having the same conductivity type as the body region 118. Protection diode 120 may be a PN junction diode (e.g., a zener diode) with a reverse breakdown voltage that is higher than a typical operating voltage that may be applied to the gate 112, but lower than the breakdown voltage of a gate dielectric between gate 112 and the channel region of IGFET 110. Protection diode 120 may be another type of diode (e.g., a Schottky diode, a discrete diode, or some other type of diode). During fabrication of the ISFET 100, plasma induced charges on the floating gate structure 130 may be discharged through the protection diode 120 into the substrate, thereby protecting the gate dielectric of the IGFET from plasma-induced damage, and thus may improve device yields and/or reliability.

ISFET 100 also may include a control gate structure 160, which is capacitively coupled (as indicated by capacitor 152) to the floating gate structure 130. The control gate structure 160 may be used during programming of ISFET 100, for example, and/or may be used to receive a bias voltage and effect movement of charge between the floating gate structure 130 and the control gate structure 160. More specifically, the control gate structure is utilized to trim the threshold voltage of the ISFET to a desired value.

Figure 2:
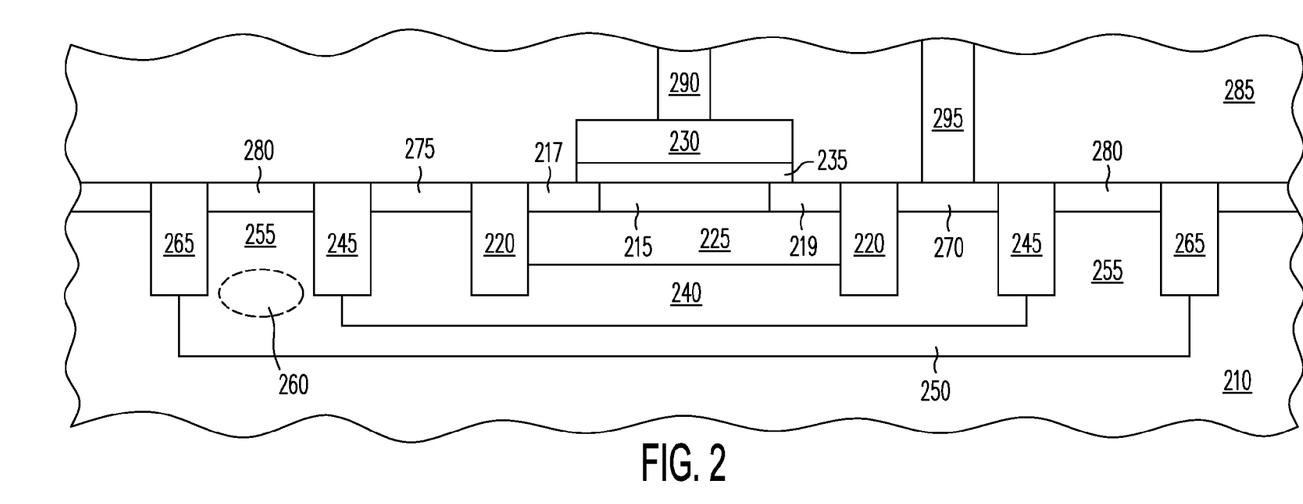
FIG. 2 is a simplified block diagram illustrating one example of a structure configured to use a buried oxide layer (BOX) associated with a channel region of a semiconductor device as a second gate dielectric, in accord with embodiments of the present invention.

FIG. 2 is a simplified block diagram illustrating one example of a structure configured to use a buried dielectric layer associated with a channel region of a semiconductor device as a second gate dielectric, in accord with embodiments of the present invention. As an example, FIG. 2 provides a transistor device structure having a p-type channel region 215 formed between n-type source and drain regions 217 and 219 over a p-type substrate 210. As will be discussed in more detail below with respect to the subsequent figures, embodiments of the present invention are not limited to transistor device structures, and can be used in conjunction with a variety of semiconductor device structures having gated channels built using a silicon-on-insulator process. Nor are embodiments limited to a particular conductivity type in the semiconductor device structure.

The transistor device is formed over a buried dielectric layer (e.g., a buried oxide layer or BOX) 225 formed of, for example, silicon dioxide. As will be discussed below, embodiments of the present invention utilize the BOX layer as a gate dielectric associated with modulating the conductivity of transistor channel 215. In addition, a traditional gate structure formed from a polysilicon or metal gate 230 and gate dielectric 235 is used to modulate the conductivity of transistor channel 215, as well. Thus, the BOX layer is associated with a second "gate" for the transistor, thereby increasing sensitivity of the transistor to a charge applied to both gate 230 and a conductive region associated with BOX 225 (e.g. doped layer 240 described below). The BOX layer is formed with a thickness of between 15 to 30 nanometers. The transistor device structure is isolated from surrounding layers by BOX layer 225 and dielectric trench regions 220 formed using a shallow trench isolation technique known in the art. While embodiments are discussed as using a buried oxide layer, the second gate dielectric is not limited to oxide layers and can be other types of dielectric layers formed using techniques known in the art.

In order for BOX layer 225 to be used as a gate dielectric, a mechanism for electrically associating the BOX layer to a sense plate is formed. The BOX layer is formed over a conductive p-well 240 that is electrically isolated from the rest of the semiconductor substrate 210. P-well 240 is laterally electrically isolated by dielectric trench regions 245 and n-type well regions 255. P-well 240 is electrically isolated on the bottom side by a deep n-well 250. Embodiments of the present invention provide for deep n-well 250 to be doped at a higher dopant concentration than n-wells 255. An n-type linking region 260 may serve to connect deep n-well 250 with n-wells 255, in some cases. Linking region 260 can be formed, for example, by using a deep implant technique using low energy with a high dose. N-wells 255 and linking region 260 are isolated from lateral regions by dielectric trench regions 265.

By electrically isolating p-well 240 in this manner, a connection can be made from the sense plate to the p-well to carry ionic charge to the BOX layer. A conductive connection is made to p-well 240 through p-type region 270, which has a corresponding p-type region 275. Typically, these regions are doped at a higher level than p-well 240 in order to provide better conductivity. P-type regions 270 and 275 are formed in the same silicon region that the transistor device structure is formed in. In addition, this same layer can be n-type doped in the regions adjacent to n-well 255 (e.g., regions 280).

As will be discussed in greater detail below, dielectric layers and metal layers are formed above the semiconductor device structure in order to provide isolation and connectivity to the sense plate and other semiconductor structures. As illustrated in FIG. 2, a dielectric layer 285 is formed over the semiconductor device structure and conductive vias 290 and 295 are formed to provide electrically conductive paths to both gate 230 and p-well 240, respectively.

As will be discussed in the figures below, in certain embodiments, conductive vias 290 and 295 are coupled, either directly or capacitively, to one or more sense plates that interact, directly or indirectly, with a fluid external to the device package. If the sense plate (or sensitive layers formed on the sense plate) interacts with ions or molecules that the sense plate is designed to interact with, a charge from those ions or molecular interaction is transmitted to gate 230 and p-well 240. In this manner, while the ionic charge modulates the conductivity of transistor channel 215 through the top gate oxide 235, interaction of the ions in p-well 240 through BOX layer 225 also modulates the channel conductivity. This combination of gate interactions serves to increase the response of the transistor to the ionic charge.

As will be appreciated by those skilled in the art, this sensitivity is further enhanced by using fully-depleted SOI processing, because the transistor channel region 215 will be thin enough to cover the entire depletion region. In order to fully appreciate the enhanced sensitivity provided by embodiments of the present invention, the channel region should be less than 40 nanometers thick, and preferably less than 10 nanometers thick.

Figure 3:
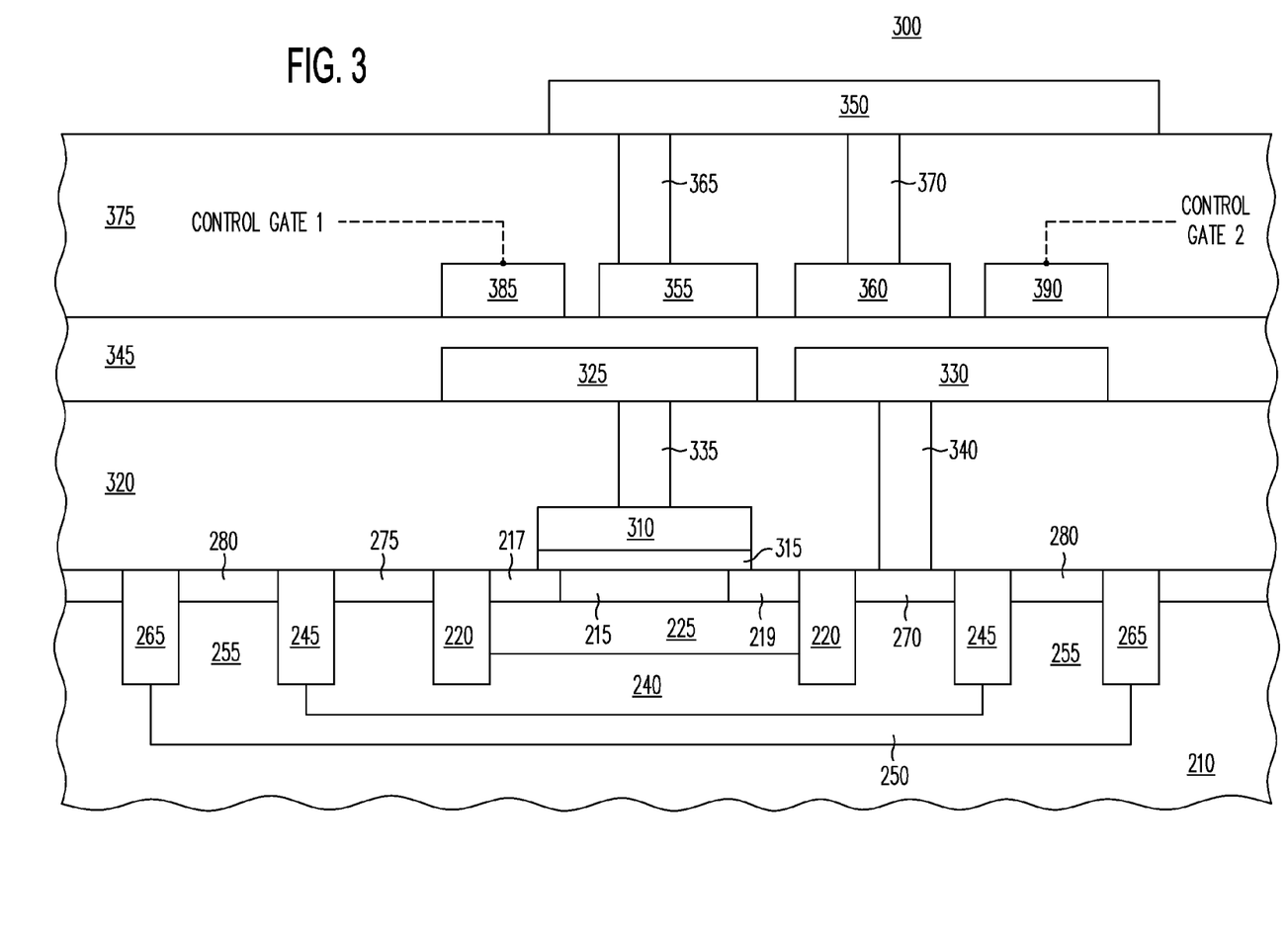
FIG. 3 is a simplified block diagram of an ISFET 300 configured in accord with embodiments of the present invention.

FIG. 3 is a simplified block diagram of an ISFET 300 configured in accord with embodiments of the present invention. For the sake of clarity, most of the portions of the ISFET that correspond to the structure discussed in FIG. 2 have the same numbering and will not be discussed here in great detail. FIG. 3 includes the same semiconductor device structure as described for FIG. 2; that is, a transistor device including a channel region 215 and source and drain regions 217 and 219.

A gate stack for the transistor device is formed above transistor channel region 215 and a portion of the source and drain regions. The gate stack includes a polysilicon or metal gate 310 formed over a gate dielectric 315. Gate dielectric 315 can include a film of silicon dioxide, silicon nitride, silicon oxynitride, a high dielectric constant ("high-k") material (e.g., dielectric constant greater than 8), or any combination thereof. The high-k material can include $Hf_aO_bN_c$, $Hf_aSi_bO_c$, $Hf_aSi_bO_cN_d$, $Hf_aZr_bO_cN_d$, $Hf_aZr_bSi_cO_dN_e$, $Hf_aZr_bO_c$, $Zr_aSi_bO_c$, $Zr_aSi_bO_cN_d$, $Zr_aO_b$, other Hf-containing or Zr-containing dielectric material, a doped version of any of the foregoing (lanthanum doped, niobium doped, etc.), or any combination thereof. As used herein, subscripts on compound materials specified with alphabetic subscripts are intended to represent the non-zero fraction of the atomic species present in that compound, and therefore, the alphabetic subscripts within a compound sum to 1. For example, in the case of $Hf_aO_bN_c$, the sum of "a," "b," and "c" is 1. Gate dielectric 315 can have a thickness in a range of approximately 1 to approximately 25 nm. Gate dielectric 315 may be thermally grown using an oxidizing or nitridizing ambient, or deposited using a conventional or proprietary chemical vapor deposition ("CVD") technique, physical vapor deposition ("PVD") technique, or any combination thereof.

In the illustrated embodiment, the gate stack forms a portion of a floating gate structure that is formed in, on, and through one or more dielectric layers 320 overlying the top surface of the substrate 210. The floating gate structure also includes a conductor 325 formed in a first metal layer, and at least one conductive via 335 electrically coupling conductor 325 to gate 310. Similarly, a conductor 330 is formed in the first metal layer, and at least one conductive via 340 is formed to electrically couple conductor 330 to p-well contact 270.

In general, dielectric layers, such as dielectric layer 320, can include a material such as silicon dioxide, silicon nitride, silicon oxynitride, or any combination of such layers to provide electrical isolation between the processed device substrate 210 and any conductive metal layers subsequently formed on or over the dielectric layers. In some cases, the dielectric layers can be thermally grown from the substrate. In other cases, the dielectric layers can be deposited. In either case, an exemplary range of thickness for the dielectric layer can be between 50 and 300 nanometers.

Conductive lines, such as conductor 330, may be formed on a dielectric layer, as illustrated in FIG. 3. Conductive lines may include a bulk portion and a cap layer. Bulk portion may generally include any conductive material, such as but not limited to doped amorphous silicon, doped polysilicon, aluminum, copper, tantalum, titanium, tungsten, or any metal alloy, nitride or silicide thereof or any material to be made conductive by subsequent implantations of dopants, such as undoped polysilicon, for example.

A sense plate structure is formed in, on, and through one or more dielectric layers 345 and 375 overlying the floating gate structures. In one embodiment, the sense plate structure includes a metal sense plate 350 that is configured to sense the concentration of a target ion or molecule in a fluid adjacent to a portion of the sense plate. Sense plate 350 can be formed in a top metal layer of ISFET 300. In order to protect the sense plate from corrosion, oxidation, or other damage, a passivation layer (not shown) may be formed over the sense plate. Alternatively, sense plate 350 is directly exposed to the environment or another type of layer can be formed over the sense plate (e.g., a gold layer, another bio-compatible metal layer, a film specific to the target ion or molecule to be detected, and the like). The sense plate structure also includes conductors 355 and 360 formed in a metal layer below the layer within which sense plate 350 is formed, along with conductive vias 365 and 370 electrically coupling conductors 355 and 360, respectively, to the sense plate.

While embodiments are discussed in terms of using a sense "plate," other fluid ion sensing structures can be used with embodiments of the present invention. For example, striped structures, honeycomb structures, slotted metal structures, and the like can be used for this purpose. For the sake of brevity, the term "sense plate" will be used below to encompass the other sensing structures, as well as plates.

As illustrated, the sense plate structure is capacitively coupled to the floating gate structures described above. Conductor 325 of the floating gate structure is aligned with conductor 355 of the sense plate structure, and conductor 330 that is coupled to p-well 240 is aligned with conductor 360 of the sense plate structure. Conductors 325 and 355, and 330 and 360, are electrically isolated from each other through a dielectric layer 345. The aligned conductors function as capacitor electrodes, while the dielectric layer is the capacitor dielectric.

Alternatively, instead of the metal-insulator-metal capacitor configuration discussed above for coupling the sense plate structure to the floating gate, a fringe capacitor configuration can be used, in which the conductors forming the capacitor are in the same metal layer, instead of stacked. Embodiments of the present invention are not limited to the method in which the sense plate is coupled to the floating gate.

Optionally, ISFET 300 may include control gate structures 385 and 390, which are capacitively coupled to the floating gate structure by being aligned with conductor 325 and 330, respectively. These control gates, formed in the same metal layer as the bottom metal of the sense plate structure, can be used to trim ISFET 300 to compensate for electrical characteristic differences between devices caused by manufacturing variations.

As illustrated in FIG. 3, as sense plate 350 comes in contact with ions or molecules the sense plate is configured to interact with, a charge builds up on the sense plate. This charge is provided, via the capacitive coupling described above, to both gate 310 and p-well 240. This charge builds up at the gate dielectric 315 and BOX layer 225, respectively, and modulates the conductivity of channel region 215. As channel region 215 becomes conductive, charge carriers can flow from source to drain regions 217 and 219, which are coupled to conductors that are not illustrated.

Figure 4:
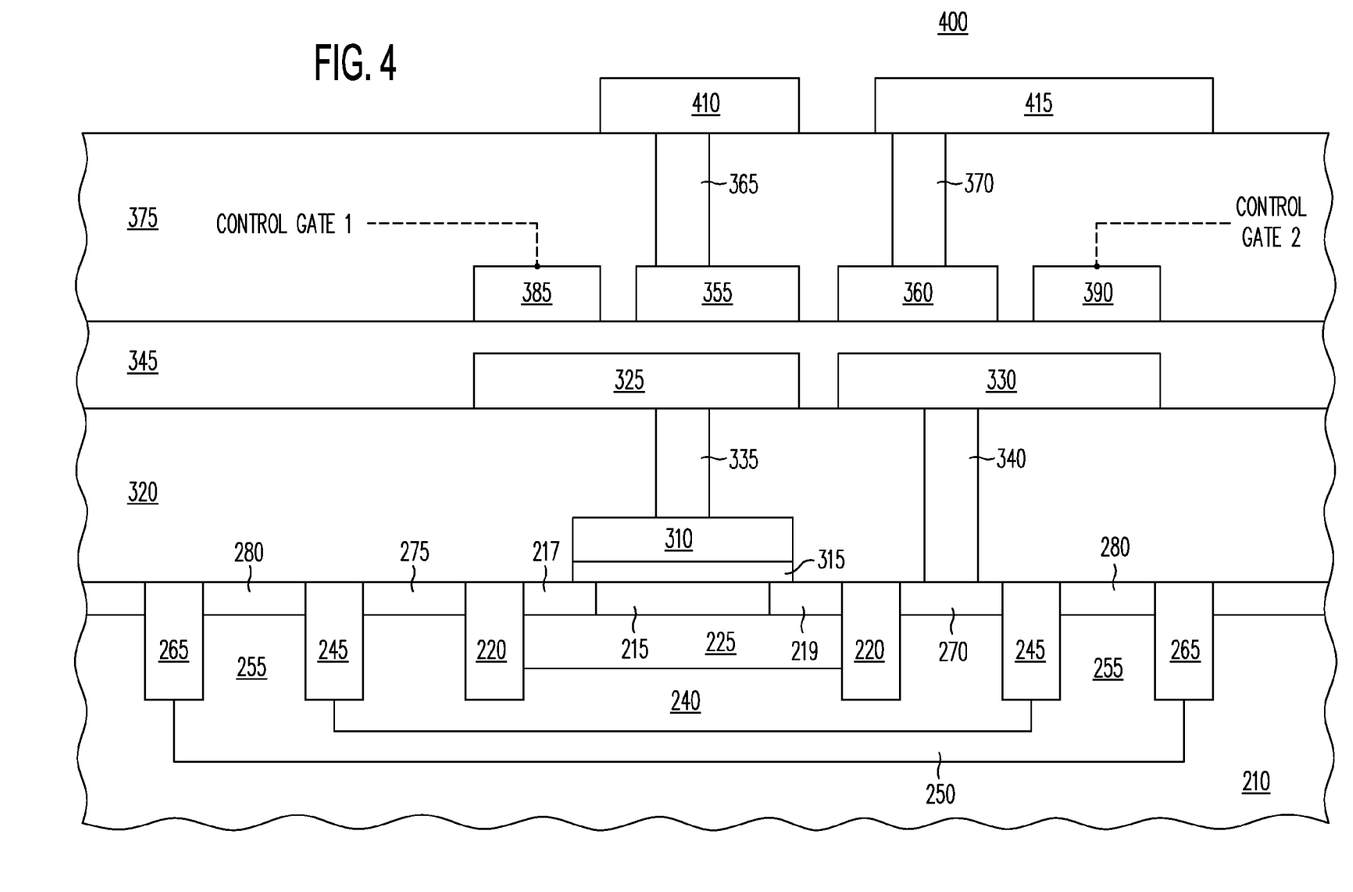
FIG. 4 is a simplified block diagram of an ISFET 400 configured in accord with embodiments of the present invention.

FIG. 4 is a simplified block diagram of an ISFET 400 configured in accord with embodiments of the present invention. For the sake of clarity, portions of the ISFET that correspond to the structures discussed in FIGS. 2 and 3 have the same numbering and will not be discussed here in great detail. FIG. 4 includes the same semiconductor device structure as described for FIGS. 2 and 3; that is, a transistor device including a channel region 215 and source and drain regions 217 and 219.

The distinction between ISFET 300 and ISFET 400 is the presence of two sense plates 410 and 415, rather than the single sense plate of ISFET 300 (in FIG. 3). Sense plate 410 is capacitively coupled to the floating gate structure coupled to gate 310. Sense plate 415 is capacitively coupled to the floating gate structure coupled to p-well 225.

Having separate sense plates 410 and 415 allows for greater flexibility in placement of the sense plates for space sensitive applications. The sense plates can be provided on the surface of the package in areas that offer the most free area, thereby increasing the overall size of the sense plates and thus sensitivity. Alternatively, the separate sense plates can be used to detect ions or molecules in fluid contact with different locations of the package, as desired.

Figure 5:
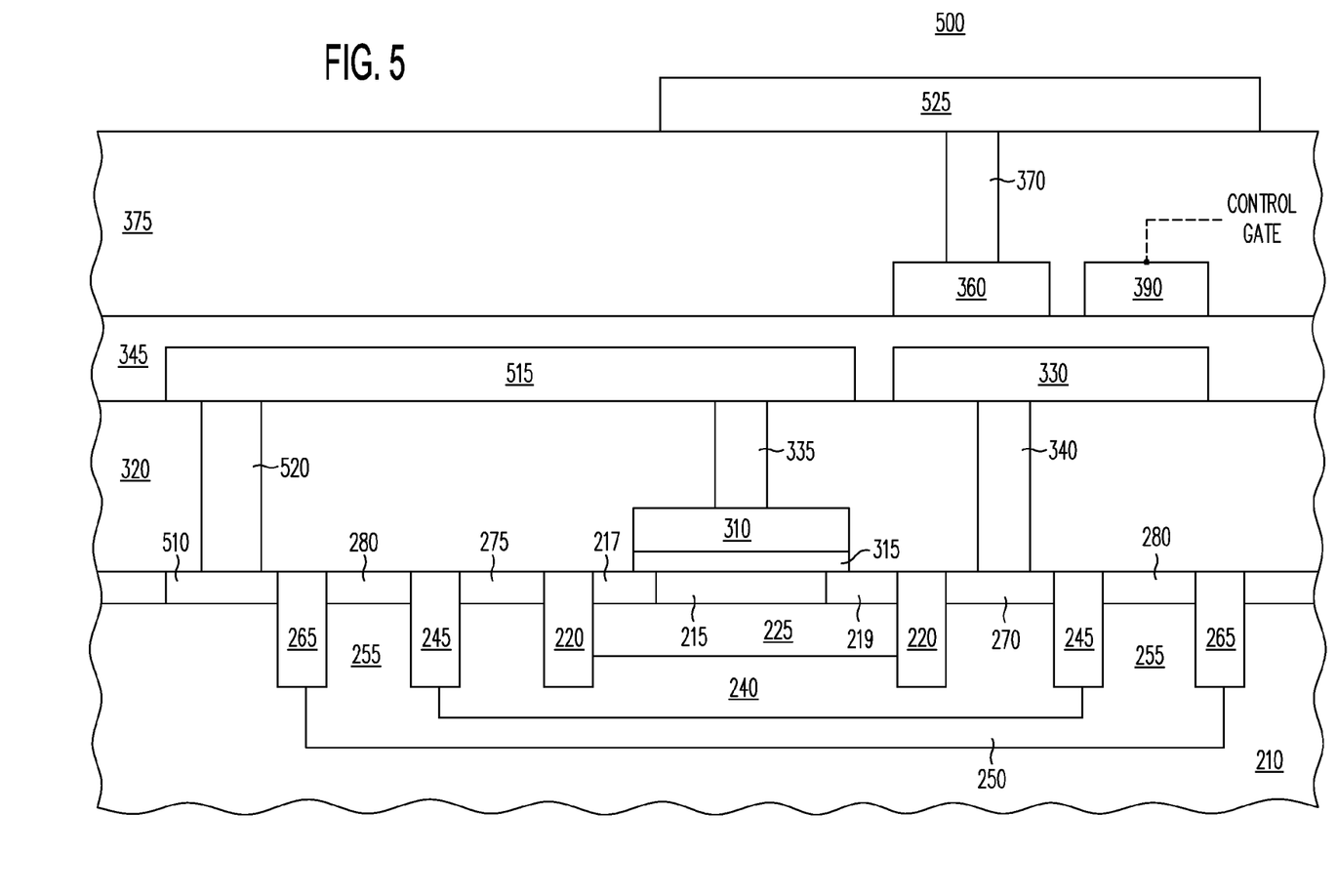
FIG. 5 is a simplified block diagram of an ISFET 500 configured in accord with embodiments of the present invention.

FIG. 5 is a simplified block diagram of an ISFET 500 configured in accord with embodiments of the present invention. Again, for the sake of clarity, portions of the ISFET that correspond to the structures discussed in FIGS. 2 and 3 have the same numbering and will not be discussed here in great detail. FIG. 5 includes the same semiconductor device structure as described for FIGS. 2 and 3; that is, a transistor device including a channel region 215 and source and drain regions 217 and 219.

A distinction between ISFET 300 and ISFET 500 is the inclusion of a protection diode electrically coupled to the floating gate structure of the ISFET. Gate 310 is coupled to a conductor 515 formed in the first metal layer described in relation to FIG. 3. Conductor 515 replaces conductor 325 illustrated in FIG. 3. Conductor 515 is electrically coupled to a protection diode formed in region 510 by a conductive via 520. The protection diode may be implemented as a PN junction diode, a zener diode, a diode in an isolated p-well, and a discrete diode electrically coupled between the floating gate structure and a well region associated with the diode. For example, a diode region of a first conductivity type can be formed in a well region of a second conductivity type, and the PN junction between the regions functions as the protection diode.

The breakdown voltage of the protection diode is higher than a typical operating voltage that may be applied to gate 310, but lower than the breakdown voltage of the gate dielectric 315. During fabrication of ISFET 500, once the floating gate structure has been formed and coupled with the protection diode, plasma induced charges on the floating gate structure generated during further fabrication processes will be discharged through the protection diode into the well region, thus protecting gate dielectric 315 from plasma-induced damage.

In this embodiment, sense plate 525 is capacitively coupled to p-well 240. Thus, the channel region conductivity modulation is only enhanced through the interaction with ion charge in p-well 240 through BOX layer 225.

Figure 6:
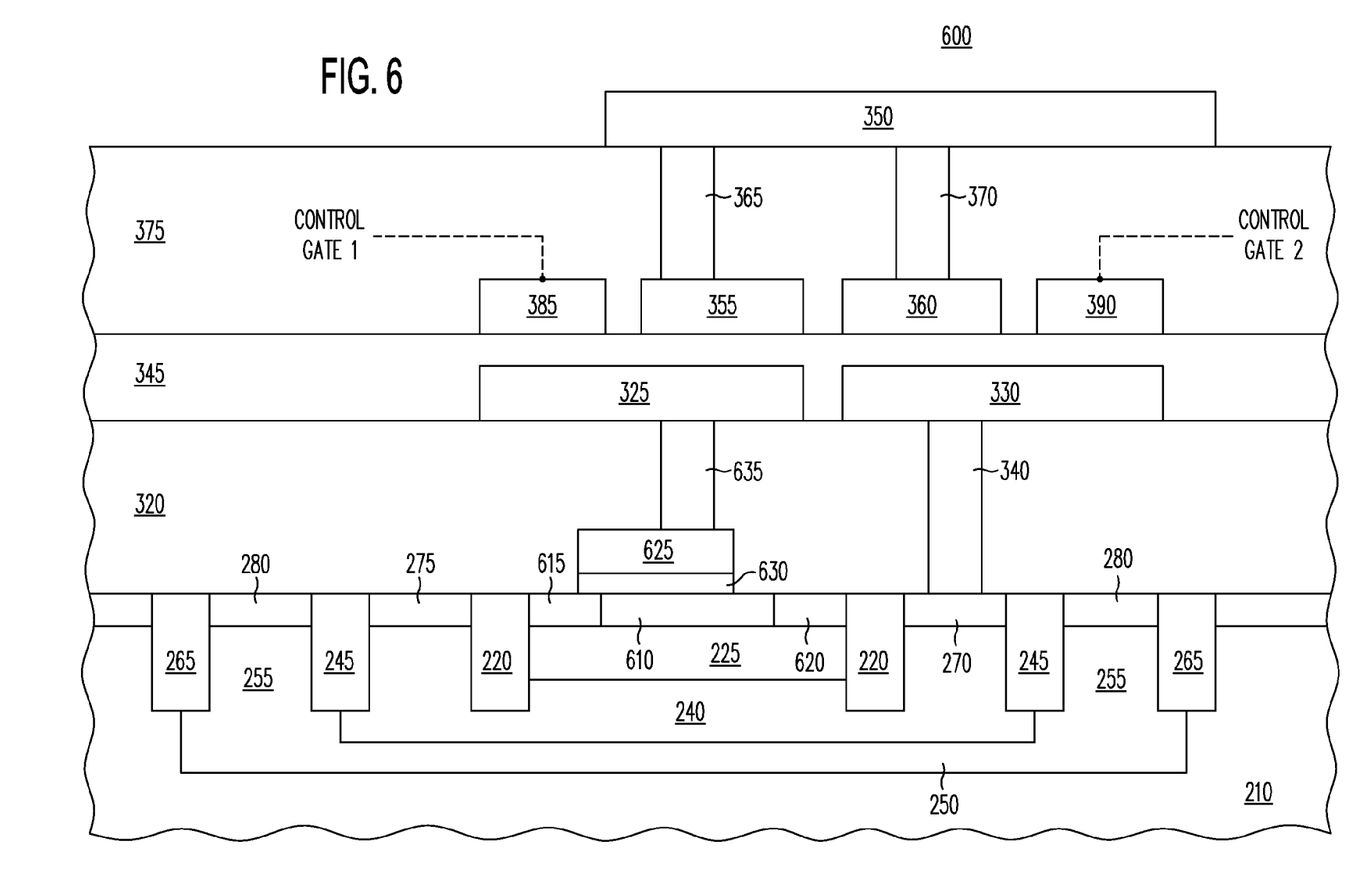
FIG. 6 is a simplified block diagram of an ion sensitive gated diode 600 configured in accord with embodiments of the present invention.

FIG. 6 is a simplified block diagram of an ion sensitive gated diode 600 configured in accord with embodiments of the present invention. For the sake of clarity, portions of the ISFET that correspond to the structure discussed in FIG. 2 have the same numbering and will not be discussed here in great detail. FIG. 6 illustrates a different semiconductor device structure than that provided in FIG. 3. Instead of a transistor device, as provided in FIG. 3, FIG. 6 provides a gated diode formed in the region adjacent to BOX layer 225.

The gated diode structure provides an anode pwell region 610 that is lightly doped with a p-type dopant. Cathode and anode contact regions 615 and 620 laterally neighbor anode pwell region 610. Cathode region 615 is heavily n-type doped while anode contact region 620 is more heavily p-type doped than is anode pwell region 610. A gate layer 625 is formed of metal or polysilicon above the anode pwell region and the cathode region, and electrically insulated from both by a gate dielectric layer 630. The buried oxide layer 225 is once again adjacent to the semiconductor device structure on the side of the channel opposite that of the gate structure.

As with the transistor structure of FIG. 3, gate 625 is electrically coupled to metal layer 325 by a conductive via 635, thereby forming a floating gate structure. The remaining structures illustrated in FIG. 6 are the same as those illustrated in FIG. 3 and perform the same or similar purpose.

When ions or molecules interact with sense plate 350, the resulting charge modulates the carrier concentration of lightly-doped anode pwell region 610 through both gate dielectric layer 630 and through BOX dielectric layer 225. As with the ISFET structure, ion interactions though the gate dielectric and the BOX layers at the same time serve to increase the sensitivity of the gated diode to the ions in the tested fluid.

Figure 7:
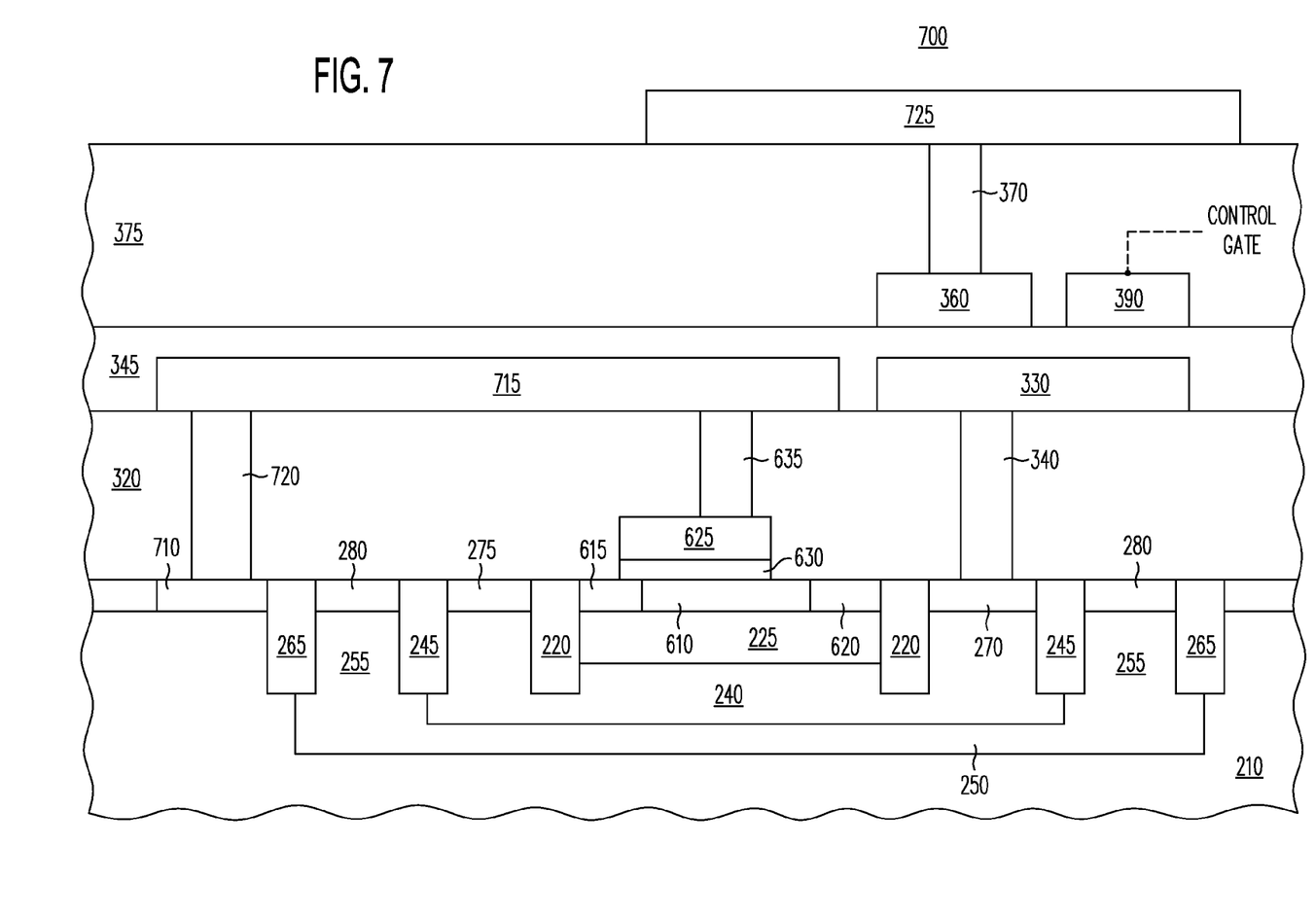
FIG. 7 is a simplified block diagram of an ion sensitive gated diode 700 configured in accord with embodiments of the present invention.

FIG. 7 is a simplified block diagram of an alternative ion sensitive gated diode 700 configured in accord with embodiments of the present invention. Again, for the sake of clarity, portions of the ion sensitive gated diode that correspond to the structures discussed in FIGS. 2, 3, and 6 have the same numbering and will not be discussed here in great detail. FIG. 7 includes the same semiconductor device structure as described for FIG. 6; that is, an ion sensitive gated diode including an anode pwell region 610, cathode region 615 and anode contact region 620.

As with FIG. 5, the distinction between ion sensitive gated diode 700 and ion sensitive gated diode 600 is inclusion of a protection diode electrically coupled to the floating gate structure of the ion sensitive gated diode. Gate 625 is coupled to a conductor 715 formed in the first metal layer described above. Conductor 715 replaces conductor 325 illustrated in FIG. 6. Conductor 715 is electrically coupled to a protection diode formed in region 710 by a conductive via 720. As with FIG. 5, the protection diode may be implemented as a PN junction diode, a zener diode, a diode in an isolated p-well, or a discrete diode that is electrically coupled between the floating gate structure and a well region associated with the diode. Such a diode is configured to protect gate dielectric 630 from plasma induced charges generated during fabrication processes, as discussed above with regard to FIG. 5.

In this embodiment, sense plate 725 is capacitively coupled to p-well 240. Thus, the anode pwell region conductivity modulation is only enhanced through the interaction with ion charge in p-well 240 through BOX layer 225.

Figure 8:
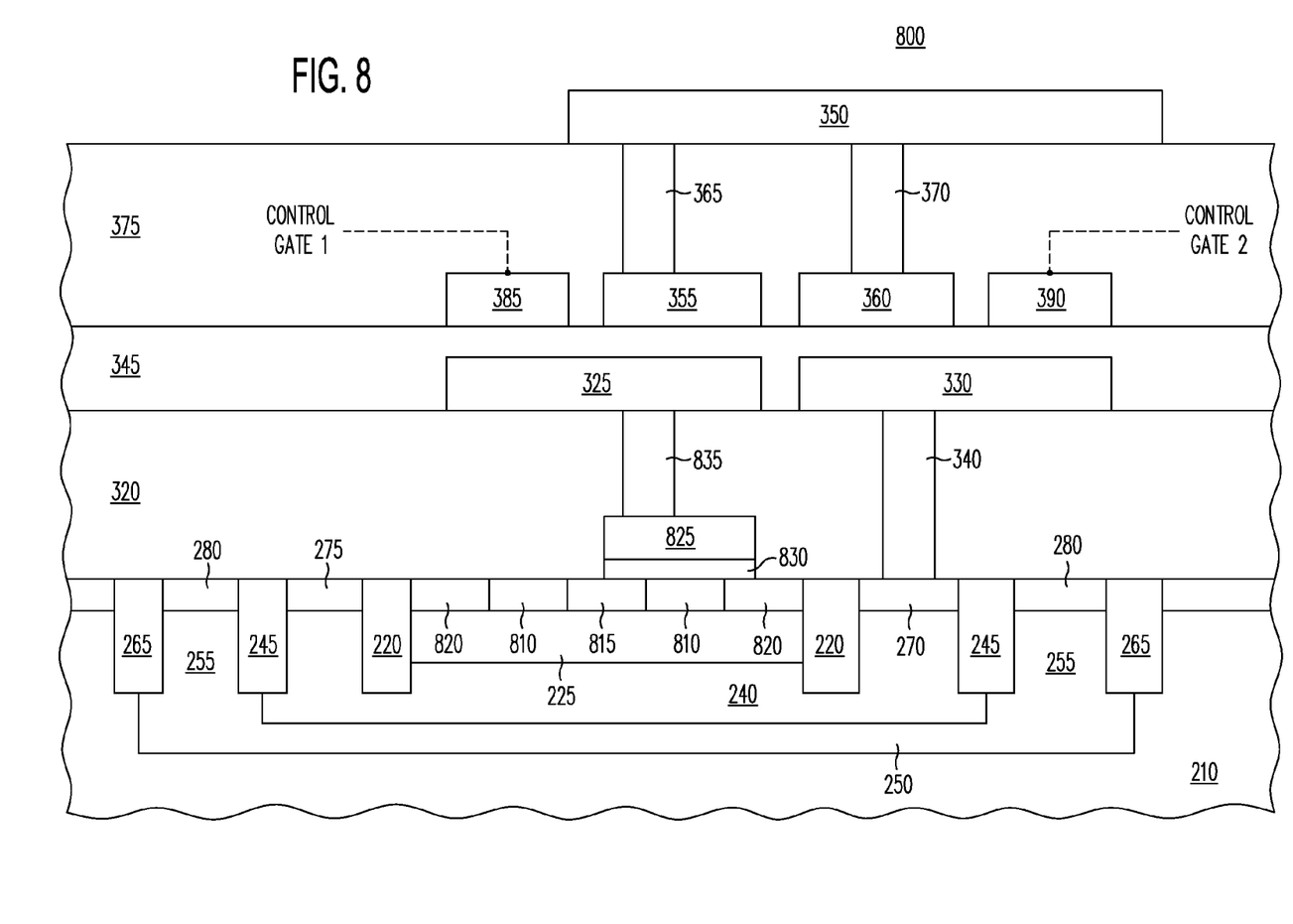
FIG. 8 is a simplified block diagram of an ion sensitive gated lateral bipolar junction transistor configured in accord with embodiments of the present invention.

FIG. 8 is a simplified block diagram of an ion sensitive gated lateral bipolar junction transistor configured in accord with embodiments of the present invention. As with the above figures, in the interests of clarity, portions of the overall structure that correspond to the structures discussed above with regard to FIGS. 2 and 3 have the same numbering and will not be discussed here in great detail.

A gated lateral bipolar junction transistor (BJT) device structure illustrated in FIG. 8 replaces the transistor device illustrated for FIG. 2. The gated lateral bipolar junction transistor includes, as is typical for such a device, a base region 810, an emitter region 815, and a collector region 820. In the illustrated embodiment, base region 810 is doped as a p-type region, while emitter 815 and collector 820 are more heavily doped (than the base region) n-type regions. The gated lateral bipolar junction transistor is arranged in a concentric ring configuration around the emitter, with the base surrounding the emitter, and the collector surrounding the base ring.

The gated lateral BJT regions 810, 815, and 820 are all formed over the BOX layer 225, which in turn overlies isolated p-well region 240 as described above. A gate 825 is formed of metal or polysilicon above portions of the base and collector regions, and a portion of the emitter region. The gate is insulated from those regions by a dielectric layer 830. As with ISFET 300, the gated lateral BJT has a floating gate by virtue of the gate stack being electrically coupled with conductor 325 by at least one conductive via 835.

As discussed above, the conductivity modulation of the base region due to ions interacting with sense plate 350 is enhanced by having not only ionic charge applied to gate 825, but also to p-well 240. The ionic charge collecting along gate dielectric 830 and BOX layer 225 increase the sensitivity of the gated lateral BJT device.

Figure 9:
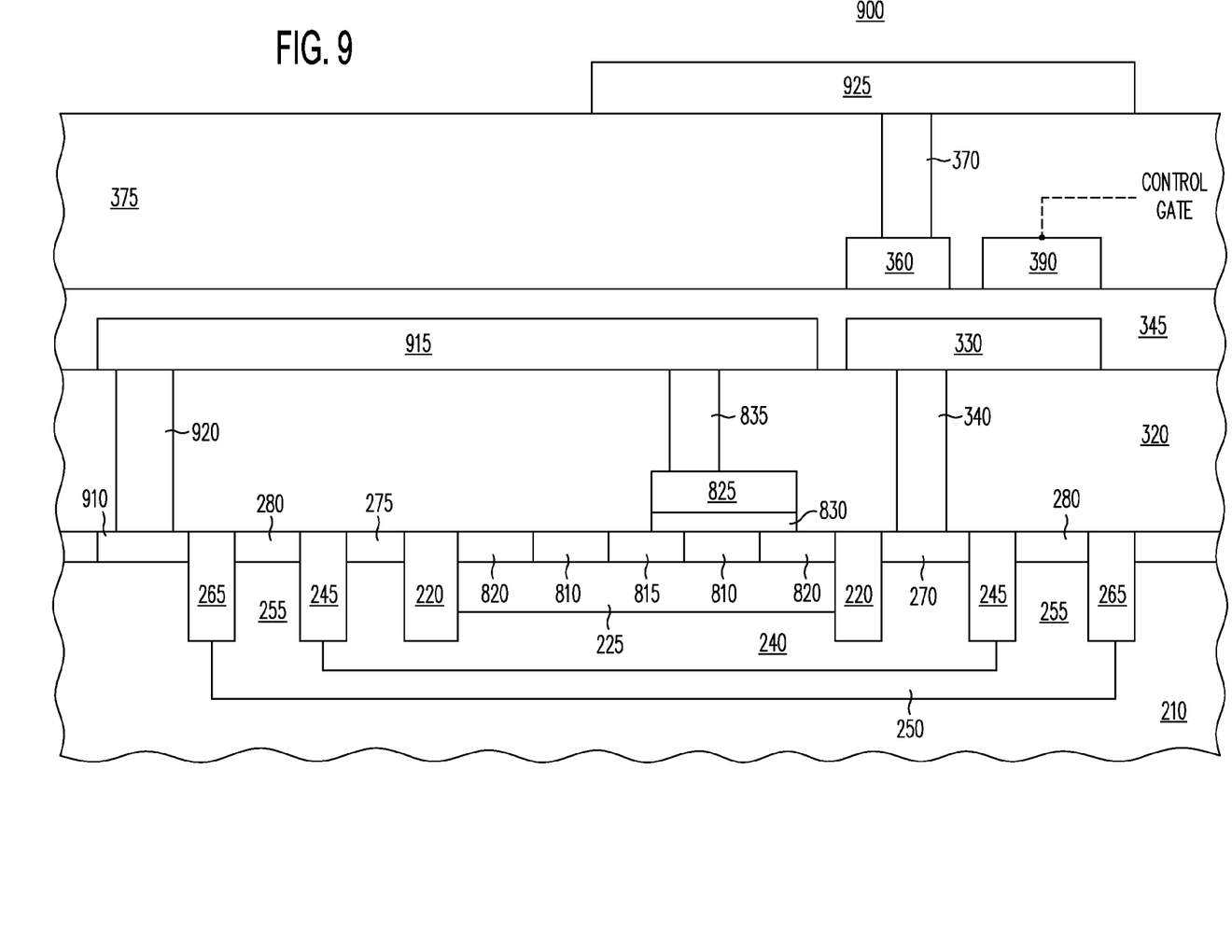
FIG. 9 is a simplified block diagram of an alternative gated lateral BJT 900 configured in accord with embodiments of the present invention.

FIG. 9 is a simplified block diagram of an alternative gated lateral BJT 900 configured in accord with embodiments of the present invention. Again, for the sake of clarity, portions of the figure that correspond to the structures discussed in FIGS. 2, 3, and 8 have the same numbering and will not be discussed here in great detail. FIG. 9 includes the same semiconductor device structure as described for FIG. 8; that is, a gated lateral BJT including a base region 810, an emitter region 815, and a collector region 820.

As with FIG. 5, the distinction between gated lateral BJT 900 and gated lateral BJT 800 is inclusion of a protection diode electrically coupled to the floating gate structure of the ion sensitive gated diode. Gate 825 is coupled to a conductor 915 formed in the first metal layer described above. Conductor 915 replaces conductor 325 illustrated in FIG. 8. Conductor 915 is electrically coupled to a protection diode formed in region 910 by a conductive via 920. As with FIG. 5, the protection diode may be implemented as a PN junction diode, or zener diode, that is electrically coupled between the floating gate structure and a well region associated with the diode. Such a diode is configured to protect gate dielectric 630 from plasma induced charges generated during fabrication processes, as discussed above with regard to FIG. 5.

In this embodiment, sense plate 925 is capacitively coupled to p-well 240. Thus, the base region conductivity modulation is only enhanced through the interaction with ion charge in p-well 240 through BOX layer 225.

Each SOI-type device discussed above benefits from the buried dielectric (e.g., BOX) layer being in contact with an isolated p-well that is coupled with a sense plate. In this manner, additional ionic charge is brought proximate to the conductivity modulated region of the device, thereby enhancing the conductivity modulation. In certain configurations, this also allows for inclusion of a protection diode, or some other ESD protection device, to help avoid fabrication damage to the gate dielectric of the device.

As will be understood, different semiconductor devices have different operating characteristics, and therefore will be appropriate for different purposes. Selection of whether to use a transistor device versus a gated diode versus a gated lateral BJT will depend upon the nature of the task the sensor is being designed for. For example, the gated lateral BJT can be configured for use in a MOSFET mode, a typical BJT mode, and a MOSFET-BJT hybrid mode. Different transconductance can be achieved using the MOSFET-BJT mode over a typical MOSFET transistor device.

By now it should be appreciated that there has been provided an improved ion sensitive semiconductor device. The device includes: a substrate having a surface; a semiconductor device layer that is formed within the surface of the substrate and which has a conductivity modulated region, a first doped region laterally adjacent to the conductivity modulated region, and a second doped region laterally adjacent to the conductivity modulated region; a gate stack formed on the surface of the substrate over a first surface of the conductivity modulated region; a buried dielectric layer formed within the substrate and adjacent to a second surface of the conductivity modulated region, where the second surface is opposite to the first surface; a conductive well region formed within the substrate beneath and adjacent to the buried dielectric layer, where the conductive well region is electrically isolated from the remainder of the substrate; and, multiple conductive structures overlying the surface of the substrate. The multiple conductive structures include a first conductor formed in first metal layer electrically coupled to the conductive well region by a first conductive via, and an ion-sensitive sense plate structure electrically coupled to the first conductor and configured to sense a concentration of a target ion or molecule in a fluid adjacent to a portion of the ion-sensitive sense plate structure.

One aspect of the above embodiment further includes a floating gate structure formed over the gate stack. The gate stack comprises a gate conductor and a gate dielectric. The floating gate structure comprises a second conductor formed in the first metal layer and is electrically coupled to the gate conductor by a second conductive via. The ion-sensitive sense plate is electrically coupled to the second conductor. In a further aspect, the first and second conductors are the same conductor. In another further aspect, the first and second conductors are separate conductors. In still another further aspect, the ion sensitive sense plate structure is one of directly electrically coupled to the first and second conductors or capacitively coupled to the first and second conductors.

Another aspect of the above embodiment further includes a protection diode structure formed in the semiconductor device layer and electrically coupled to the substrate, and a floating gate structure formed over the gate stack. The gate stack includes a gate conductor and a gate dielectric. The floating gate structure also includes a second conductor formed in the first metal layer and electrically coupled to the gate conductor by a second conductive via. The protection diode structure is electrically coupled to the second conductor by a third conductive via. In a further aspect, the ion sensitive sense plate structure is electrically coupled to the first conductor and not electrically coupled to the second conductor. In another further aspect, the ion sensitive sense plate structure is one of directly electrically coupled to the first conductor or capacitively coupled to the first conductor.

Another aspect of the above embodiment further provides that the semiconductor device is an ion sensitive field effect transistor. In this aspect, the first doped region includes a dopant of a first conductivity type, the second doped region includes a dopant of the first conductivity type, the conductivity modulated region includes a dopant of a second conductivity type, and the conductive well region includes a dopant of the second conductivity type. Another aspect of the above embodiment further provides that the semiconductor device is an ion sensitive gated diode. In this aspect, the first doped region includes a dopant of a first conductivity type, the second doped region includes a dopant of a second conductivity type, the conductivity modulated region includes a dopant of the second conductivity type, and the conductive well region includes a dopant of the second conductivity type.

Another aspect of the above embodiment further provides that the semiconductor device is an ion-sensitive gated lateral bipolar junction transistor. In this aspect, the first doped region includes a dopant of a first conductivity type and is a emitter, the second doped region includes a dopant of the first conductivity type and is a collector, the conductivity modulated region includes a dopant of a second conductivity type, the conductive well region includes a dopant of the second conductivity type, and the emitter, conductivity modulated region, and collector form concentric regions with the emitter in the center, the conductivity modulated region surrounding the emitter, and the collector surrounding the conductivity modulated region.

Another embodiment of the present invention provides a method of forming an ion sensitive semiconductor device structure. The method includes: forming a first well region of a first conductivity type in a substrate of a second conductivity type; forming a second well region of a second conductivity type within the first well region; forming a buried dielectric layer within the second well region; forming a semiconductor device layer within the substrate, wherein the semiconductor device layer comprises a conductivity modulated region, a first doped region disposed laterally adjacent to the conductivity modulated region, and a second doped region disposed laterally adjacent to the conductivity modulated region, the semiconductor device layer is disposed above each of the first well region, the second well region, and the buried dielectric layer, and the conductivity modulated region is disposed above and adjacent to the buried dielectric layer; electrically isolating the second doped region from the remainder of the semiconductor device layer by forming a second trench extending from the surface of the semiconductor device layer to a depth within the second well region, but not extending to the first well region; and, electrically coupling the second doped region to an ion-sensitive sense plate structure that is configured to sense a concentration of a target ion or molecule in a fluid adjacent to a portion of the ion-sensitive sense plate structure.

In one aspect of the above embodiment, the method further includes: forming a third trench extending from the surface of the semiconductor device layer to a depth within the second well region along a first boundary of the first and second well regions; forming a fourth trench extending from the surface of the semiconductor device layer to a depth within the second well region along a second boundary of the first and second well regions; forming a fifth trench extending from the surface of the semiconductor device layer along a first boundary of the first well region with the remainder of the substrate; forming a sixth trench extending from the surface of the semiconductor device layer along a second boundary of the first well region with the remainder of the substrate; and, forming a dielectric within the first, second, third, fourth, fifth, and sixth trenches.

In another aspect of the above embodiment, the method further includes: forming a first dielectric layer above and in contact with at least a portion of the semiconductor device layer; forming a first metal layer above the first dielectric layer, wherein the first metal layer comprises a first conductor; forming a first conductive via through the first dielectric layer, wherein the first conductive via is configured to electrically couple the first conductor with the second doped region; forming a second dielectric layer above and in contact with the first metal layer; forming a second metal layer above the second dielectric layer, wherein the second metal layer comprises a second conductor aligned over the first conductor; forming a third dielectric layer above and in contact with the second metal layer; forming an ion-sensitive sense plate above the third dielectric layer; and, forming a second conductive via through the third dielectric layer. The second conductive via is configured to electrically couple the ion-sensitive sense plate with the second conductor. The second conductor is capacitively coupled with the first conductor. In a further aspect, the method also includes forming a gate dielectric and a gate over the conductivity modulated region, forming a third conductor in the first metal layer, and forming a third conductive via through the first dielectric layer. The third conductive via is configured to electrically couple the third conductor with the gate. In a still further aspect, the second metal layer further includes a fourth conductor, and the method further includes forming a fourth conductive via through the third dielectric layer. The fourth conductive via is configured to electrically couple the ion-sensitive sense plate with the fourth conductor. The fourth conductor is aligned over the third conductor, and the fourth conductor is capacitively coupled with the third conductor. In another further aspect, the method further includes forming a protection diode circuit in a portion of the semiconductor device layer, and forming a fifth conductive via through the first dielectric layer, where the fifth conductive via is configured to electrically couple the third conductor with the protection diode circuit.

In another aspect of the above embodiment, the method further includes: doping the first doped region with a dopant of a first conductivity type; doping the second doped region with a dopant of the first conductivity type; doping the conductivity modulated region with a dopant of a second conductivity type; doping the second well region with a dopant of the second conductivity type; and doping first well region with a dopant of the first conductivity type.

In another aspect of the above embodiment, the method further includes: doping the first doped region with a dopant of a first conductivity type; doping the second doped region with a dopant of a second conductivity type; doping the conductivity modulated region with a dopant of the second conductivity type; doping the second well region with a dopant of the second conductivity type; and doping the first well region with a dopant of the first conductivity type.

In still another aspect of the above embodiment, the method further includes: doping the first doped region with a dopant of a first conductivity type and is a emitter; doping the second doped region with a dopant of the first conductivity type and is a collector; doping the conductivity modulated region with a dopant of a second conductivity type; doping the second well region with a dopant of the second conductivity type; and forming the emitter, conductivity modulated region, and collector as concentric regions with the emitter in the center, the conductivity modulated region surrounding the emitter, and the collector surrounding the conductivity modulated region.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

Although the invention has been described with respect to specific conductivity types or polarity of potentials, skilled artisans appreciated that conductivity types and polarities of potentials may be reversed wherein a p-type region becomes an n-type region and vice versa. Alternatively, the particular regions illustrated may be more generally referred to as of a "first conductivity type" and a "second conductivity type," wherein the first conductivity type may be either n or p type and the second opposite conductivity type is then either p or n type, as so forth. Further, for convenience of explanation and not intended to be limiting, various embodiments of the present invention are described herein as silicon semiconductors, but persons of skill in the art will understand the invention is not limited to silicon but applies to a wide variety of semiconductor materials. Non-limiting examples are other type IV semiconductor materials, as well as type III-V and II-VI semiconductor materials, organic semiconductor materials, and combinations thereof, in semiconductor-on-insulator form. Such materials may be single-crystal or poly-crystalline or amorphous or combinations thereof.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

The term "coupled," as used herein, is not intended to be limited to a direct coupling or a mechanical coupling.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Unless stated otherwise, terms such as "first" and "second" are used to arbitrarily distinguish between the elements such terms describe. Thus, these terms are not necessarily intended to indicate temporal or other prioritization of such elements.

What is claimed is:

1. An ion sensitive semiconductor device comprising:
    a substrate comprising a surface;
    a semiconductor device layer, formed within the surface of the substrate, and comprising a conductivity modulated region, a first doped region disposed laterally adjacent to the conductivity modulated region, and a second doped region disposed laterally adjacent to the conductivity modulated region;
    a gate stack formed on the surface of the substrate and over a first surface of the conductivity modulated region;
    a buried dielectric layer formed within the substrate and adjacent to a second surface of the conductivity modulated region, wherein the second surface is opposite to the first surface;
    a conductive well region formed within the substrate beneath and adjacent to the buried dielectric layer, wherein the conductive well region is electrically isolated from the remainder of the substrate;
    multiple conductive structures overlying the surface of the substrate, wherein the multiple conductive structures comprise
        a first conductor formed in first metal layer electrically coupled to the conductive well region by a first conductive via, and
        an ion-sensitive sense plate structure electrically coupled to the first conductor and configured to sense a concentration of a target ion or molecule in a fluid adjacent to a portion of the ion-sensitive sense plate structure.

2. The ion sensitive semiconductor device of claim 1 further comprising:
    a floating gate structure formed over the gate stack, wherein
        the gate stack comprises a gate conductor and a gate dielectric,
        the floating gate structure comprises a second conductor formed in the first metal layer and is electrically coupled to the gate conductor by a second conductive via, and
        the ion-sensitive sense plate is electrically coupled to the second conductor.

3. The ion sensitive semiconductor device of claim 2 wherein the first and second conductors are the same conductor.

4. The ion sensitive semiconductor device of claim 2 wherein the first and second conductors are separate conductors.

5. The ion sensitive semiconductor device of claim 2 wherein the ion sensitive sense plate structure is one of directly electrically coupled to the first and second conductors or capacitively coupled to the first and second conductors.

6. The ion sensitive semiconductor device of claim 1 further comprising:
    a protection diode structure formed in the semiconductor device layer and electrically coupled to the substrate; and
    a floating gate structure formed over the gate stack, wherein
        the gate stack comprises a gate conductor and a gate dielectric,
        the floating gate structure comprises a second conductor formed in the first metal layer and is electrically coupled to the gate conductor by a second conductive via, and
        the protection diode structure is electrically coupled to the second conductor by a third conductive via.

7. The ion sensitive semiconductor device of claim 6 wherein the ion sensitive sense plate structure is electrically coupled to the first conductor and not electrically coupled to the second conductor.

8. The ion sensitive semiconductor device of claim 6 wherein the ion sensitive sense plate structure is one of directly electrically coupled to the first conductor or capacitively coupled to the first conductor.

9. The ion sensitive semiconductor device of claim 1, wherein the semiconductor device is an ion sensitive field effect transistor and
    the first doped region comprises a dopant of a first conductivity type,
    the second doped region comprises a dopant of the first conductivity type,
    the conductivity modulated region comprises a dopant of a second conductivity type, and the conductive well region comprises a dopant of the second conductivity type.

10. The ion sensitive semiconductor device of claim 1, wherein the semiconductor device is an ion sensitive gated diode and
the first doped region comprises a dopant of a first conductivity type,
the second doped region comprises a dopant of a second conductivity type,
the conductivity modulated region comprises a dopant of the second conductivity type, and
the conductive well region comprises a dopant of the second conductivity type.

11. The ion sensitive semiconductor device of claim 1, wherein the semiconductor device is an ion sensitive gated lateral bipolar junction transistor, and
the first doped region comprises a dopant of a first conductivity type and is a emitter,
the second doped region comprises a dopant of the first conductivity type and is a collector,
the conductivity modulated region comprises a dopant of a second conductivity type,
the conductive well region comprises a dopant of the second conductivity type, and
the emitter, conductivity modulated region, and collector form concentric regions with the emitter in the center, the conductivity modulated region surrounding the emitter, and the collector surrounding the conductivity modulated region.

12. A method of forming an ion sensitive semiconductor device structure, the method comprising:
forming a first well region of a first conductivity type in a substrate of a second conductivity type;
forming a second well region of a second conductivity type within the first well region;
forming a buried dielectric layer within the second well region;
forming a semiconductor device layer within the substrate, wherein
the semiconductor device layer comprises a conductivity modulated region, a first doped region disposed laterally adjacent to the conductivity modulated region, and a second doped region disposed laterally adjacent to the conductivity modulated region,
the semiconductor device layer is disposed above each of the first well region, the second well region, and the buried dielectric layer, and
the conductivity modulated region is disposed above and adjacent to the buried dielectric layer;
electrically isolating the second doped region from the remainder of the semiconductor device layer by forming a second trench extending from the surface of the semiconductor device layer to a depth within the second well region, but not extending to the first well region; and
electrically coupling the second doped region to an ion-sensitive sense plate structure that is configured to sense a concentration of a target ion or molecule in a fluid adjacent to a portion of the ion-sensitive sense plate structure.

13. The method of claim 12 further comprising:
forming a third trench extending from the surface of the semiconductor device layer to a depth within the second well region along a first boundary of the first and second well regions;
forming a fourth trench extending from the surface of the semiconductor device layer to a depth within the second well region along a second boundary of the first and second well regions;
forming a fifth trench extending from the surface of the semiconductor device layer along a first boundary of the first well region with the remainder of the substrate;
forming a sixth trench extending from the surface of the semiconductor device layer along a second boundary of the first well region with the remainder of the substrate; and
forming a dielectric within the first, second, third, fourth, fifth, and sixth trenches.

14. The method of claim 12 wherein said electrically coupling the second doped region to the ion-sensitive sense plate further comprises:
forming a first dielectric layer above and in contact with at least a portion of the semiconductor device layer;
forming a first metal layer above the first dielectric layer, wherein the first metal layer comprises a first conductor;
forming a first conductive via through the first dielectric layer, wherein the first conductive via is configured to electrically couple the first conductor with the second doped region;
forming a second dielectric layer above and in contact with the first metal layer;
forming a second metal layer above the second dielectric layer, wherein the second metal layer comprises a second conductor aligned over the first conductor;
forming a third dielectric layer above and in contact with the second metal layer;
forming an ion-sensitive sense plate above the third dielectric layer; and
forming a second conductive via through the third dielectric layer, wherein
the second conductive via is configured to electrically couple the ion-sensitive sense plate with the second conductor, and
the second conductor is capacitively coupled with the first conductor.

15. The method of claim 14 further comprising:
forming a gate dielectric and a gate over the conductivity modulated region;
forming a third conductor in the first metal layer;
forming a third conductive via through the first dielectric layer, wherein the third conductive via is configured to electrically couple the third conductor with the gate.

16. The method of claim 15 wherein the second metal layer further comprises a fourth conductor, and the method further comprises:
forming a fourth conductive via through the third dielectric layer, wherein
the fourth conductive via is configured to electrically couple the ion-sensitive sense plate with the fourth conductor,
the fourth conductor is aligned over the third conductor, and
the fourth conductor is capacitively coupled with the third conductor.

17. The method of claim 15 further comprising:
forming a protection diode circuit in a portion of the semiconductor device layer;
forming a fifth conductive via through the first dielectric layer, wherein the fifth conductive via is configured to electrically couple the third conductor with the protection diode circuit.

18. The method of claim 12 further comprising:
doping the first doped region with a dopant of a first conductivity type;
doping the second doped region with a dopant of the first conductivity type;
doping the conductivity modulated region with a dopant of a second conductivity type;
doping the second well region with a dopant of the second conductivity type; and
doping first well region with a dopant of the first conductivity type.

19. The method of claim 12 further comprising:
doping the first doped region with a dopant of a first conductivity type;
doping the second doped region with a dopant of a second conductivity type;
doping the conductivity modulated region with a dopant of the second conductivity type;
doping the second well region with a dopant of the second conductivity type; and
doping the first well region with a dopant of the first conductivity type.

20. The method of claim 12 further comprising:
doping the first doped region with a dopant of a first conductivity type and is a emitter;
doping the second doped region with a dopant of the first conductivity type and is a collector;
doping the conductivity modulated region with a dopant of a second conductivity type;
doping the second well region with a dopant of the second conductivity type; and
forming the emitter, conductivity modulated region, and collector as concentric regions with the emitter in the center, the conductivity modulated region surrounding the emitter, and the collector surrounding the conductivity modulated region.

\* \* \* \* \*